(12) United States Patent
Persson

(10) Patent No.: US 7,900,631 B2
(45) Date of Patent: Mar. 8, 2011

(54) DEVICE FOR HOLDING A TRACHEAL CANNULA

(75) Inventor: Jan-Ove Persson, Höör (SE)

(73) Assignee: Atos Medical AB, Horby (SE)

( * ) Notice: Subject to any disclaimer, the term of this patent is extended or adjusted under 35 U.S.C. 154(b) by 0 days.

(21) Appl. No.: 10/844,409

(22) Filed: May 13, 2004

(65) Prior Publication Data

US 2004/0226564 A1 Nov. 18, 2004

(51) Int. Cl.
*A61M 16/00* (2006.01)
*A62B 9/06* (2006.01)

(52) U.S. Cl. .............................. 128/207.14; 128/207.17

(58) Field of Classification Search ............ 128/207.17, 128/200.26, 207.14, DIG. 26; 604/179, 180
See application file for complete search history.

(56) References Cited

U.S. PATENT DOCUMENTS

| | | | | |
|---|---|---|---|---|
| 3,713,448 A * | 1/1973 | Arrott | ...................... | 128/207.17 |
| 4,122,857 A * | 10/1978 | Haerr | ........................... | 604/180 |
| 4,142,527 A * | 3/1979 | Garcia | ........................... | 604/180 |
| 4,313,437 A * | 2/1982 | Martin | ..................... | 128/207.17 |
| 4,331,144 A * | 5/1982 | Wapner | ..................... | 128/207.17 |
| 4,449,527 A * | 5/1984 | Hinton | ..................... | 128/207.17 |
| 4,520,813 A * | 6/1985 | Young | ..................... | 128/207.17 |
| 5,221,265 A * | 6/1993 | List | .............................. | 604/180 |
| 5,237,988 A * | 8/1993 | McNeese | ................ | 128/207.17 |
| 5,292,312 A * | 3/1994 | Delk et al. | ................... | 604/180 |
| 5,357,952 A * | 10/1994 | Schuster et al. | ......... | 128/207.17 |
| 5,490,504 A * | 2/1996 | Vrona et al. | ............ | 128/207.17 |
| 5,529,062 A * | 6/1996 | Byrd | ........................ | 128/207.17 |
| 5,671,732 A * | 9/1997 | Bowen | ..................... | 128/207.17 |
| 5,676,137 A * | 10/1997 | Byrd | ........................ | 128/207.17 |
| 5,743,885 A * | 4/1998 | Hoerby | ......................... | 604/180 |
| 5,797,394 A * | 8/1998 | Boyd | ........................ | 128/207.17 |
| 5,868,132 A * | 2/1999 | Winthrop et al. | ........ | 128/207.14 |
| 5,924,421 A * | 7/1999 | Rosbrook et al. | ....... | 128/207.14 |
| 6,009,872 A * | 1/2000 | Delaplane et al. | ....... | 128/207.17 |
| 6,050,263 A * | 4/2000 | Choksi et al. | ............ | 128/207.14 |
| 6,612,309 B1 * | 9/2003 | Ancona | ..................... | 128/207.17 |

* cited by examiner

*Primary Examiner* — Tatyana Zalukaeva
*Assistant Examiner* — Kristen C Matter
(74) *Attorney, Agent, or Firm* — Rader, Fishman & Grauer PLLC

(57) ABSTRACT

The invention relates to a device for supporting and retaining a tracheal cannula or a similar appliance on a person's neck. The device comprises wings on the cannula projecting in opposite directions from the cannula. Fastening means connected with the wings comprises an element having an adhesive surface for attachment to the skin of the neck.

17 Claims, 4 Drawing Sheets

DEVICE FOR HOLDING A TRACHEAL CANNULA

BACKGROUND OF THE INVENTION

1. Field of the Invention

The invention relates to a device for supporting and retaining a tracheal cannula or similar appliance on a person's neck in connection with a tracheostoma, comprising two wings on the cannula projecting in opposite directions from the cannula, and fastening means connected with the wings.

2. Description of Prior Art

Persons who are tracheostomized or laryngectomized have gone through a surgical operation in which an opening, stoma, has been made in the person's neck in order to create a direct connection with trachea (windpipe). The cause for such an operation may be a physical injury against the neck at an accident, sleep apnea of overweight persons, lung disease, or removal of the larynx due to cancer therein (laryngectomy).

On all tracheostomized persons and many of the laryngectomized persons it is necessary to keep the stoma open by means of some sort of stent, usually a tracheal cannula e.g. as those disclosed in U.S. Pat. No. 5,471,980 A, U.S. Pat. No. 4,331,144 A and DE 298 06 659 U1. As shown therein the cannula is a substantially right-angled tube open at both ends.

The tracheal cannula is exposed to axial forces, which particularly at coughing and speech tend to cause outward movement of the cannula in the stoma causing irritation of mucous membranes and leakage. In the worst case the cannula may move completely out of the stoma. In order that the cannula shall remain in position it is held by means of a neck strap which can be of different types varying from simple cotton straps which are connected with the cannula and are tied round the neck by a knot, to more advanced straps as those disclosed e.g. in U.S. Pat. No. 5,471,980 A and U.S. Pat. No. 4,331,144 A.

Referring to FIG. 1 on the accompanying drawings a tracheal cannula 10 is supported in the stoma by means of a simple strap 11 round the person's neck, the strap 11 being connected with diametrically opposite wings 12 on the cannula and being knotted round the neck at 13. The axis of the portion of the cannula which extends through the stoma is indicated by a dot-and-dash line 14, and the direction of the strap is indicated by a dot-and-dash line 15 the angle between lines 14 and 15 being designated φ.

Many persons find it annoying to have a strap round the neck. It causes sweating, the strap gets dirty, head movements are impeded, the strap lands on the wound directly after a laryngectomy etc. The most important drawback is, however, that there is an unfavourable angle φ between the strap and the cannula at low-positioned stomas as shown in FIG. 1 which causes an unsatisfactory fixation of the cannula. In extreme cases the cannula will not be kept in the intended position but will be withdrawn when the pulling force acts from above in the direction of line 15.

US 2001/0035182 A1 discloses an adapter which is partly inserted into a tracheostoma and has a spacer which is configured to abut the skini of the user proximate the tracheostoma when the adapter is in position during use. The spacer can include an adhesive formed thereon so that the adapter can be adhesively secured to and released from the skin in an annular region around the tracheostoma. However, the central positioning of an adhesive connection proximate the tracheostoma does not function in practice because the adhesive will deteriorate very rapidly when in contact with mucus secret and substantial humid secretion through the human tissues. Moreover, an adhesive connection cannot be used proximate the tracheostoma when the skin around the tracheostoma is very sensible particularly after surgery or radiation. Generally, it should be avoided to expose the skin proximate the tracheostoma to unnecessary strain. Many patients remove the tracheal cannula several times each day for cleaning. An adhesive connection proximate the tracheostoma under these circumstances would rapidly destroy the tissues around the tracheostoma.

BRIEF SUMMARY OF THE INVENTION

A primary object of the invention is to overcome the drawbacks and shortcomings accounted for, and this is to be achieved by providing a device of the kind reffered to above, which is characterized in that the fastening means comprises an adhesive element having an adhesive surface, distanced from the cannulla, for attachment of the device to the skin of the neck a space being provided between the adhesive surface and the tracheostoma.

By this attachment at each side of the stoma and close to the stoma the tracheal cannula is effectively anchored in the intended position and is prevented from movement in the stoma, also in case the stoma is located at a low level. The unpleasant feeling of having something that has a tight fitting round the neck is completely eliminated. The fixation of the cannula is more hygienic than that provided by prior art devices. Since the adhesive surface is spaced from the tracheostoma the sensible tissues around the tracheostoma are not exposed to harsh and painful treatment when the tracheal cannula is removed from and again inserted into the tracheostoma.

BRIEF DESCRIPTION OF THE DRAWINGS

Illustrative embodiments of the invention will be described in more detail below with reference to FIGS. 2 to 11 on the accompanying drawings in which FIG. 1 discloses a prior art tracheal cannula supported in a stoma by means of a simple strap.

DETAILED DESCRIPTION OF THE INVENTION

Figure 1:
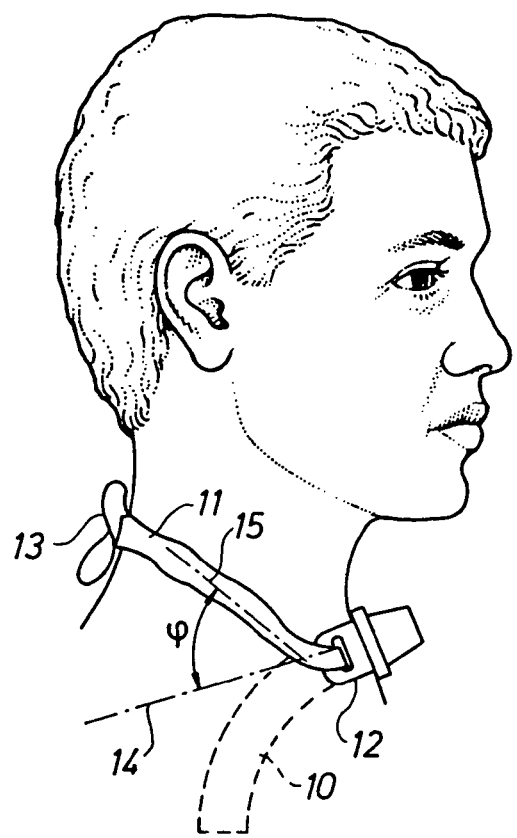
Figure 2:
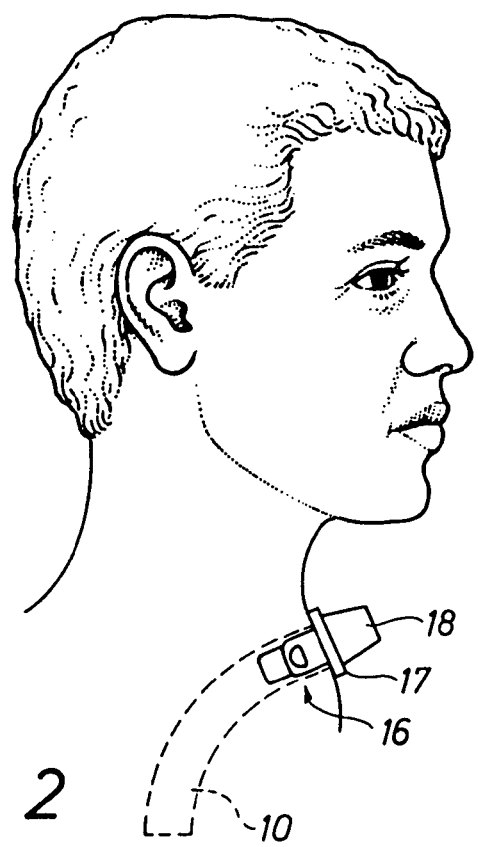
FIG. 2 discloses a tracheal cannula supported in the stoma by means of the device of the invention.
Figure 3:
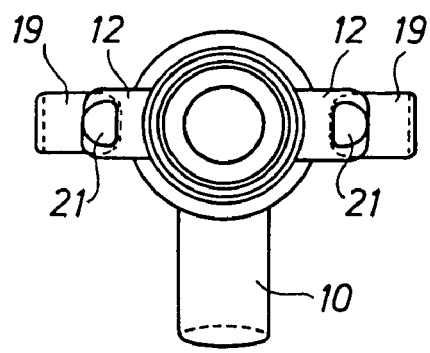
FIG. 3 is a front view of an illustrative embodiment of the device of the invention.
Figure 4:
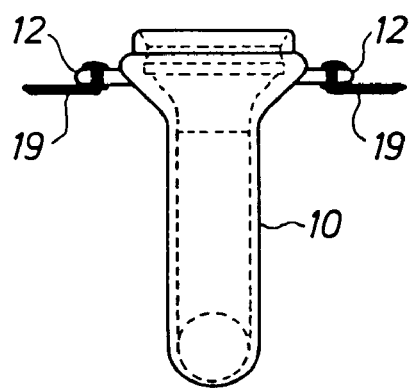
FIG. 4 is a plan view of the device in FIG. 3.

FIG. 2 in the drawings discloses a conventional tracheal cannula 10 as attached by means of the device of the invention the device being generally designated 16. The cannula has a circumferential flange 17 abutting the skin of the neck around the stoma, and forms a connection cone 18 for the attachment of an appliance such as a stoma valve and/or a heat and moisture exchanger communicating with trachea through cannula 10. Wings 12 projecting from the cannula in diametrically opposite directions are formed as individual flaps but can also be integrated as a circumferential flange on the cannula which may be made of a soft plastic material such as polyvinylchloride or silicone of medical grade. Tracheal cannulas for laryngectomized persons are made softer and have no connection cone.

Referring to FIGS. 3 to 9 a hook 19 of plastic material forms a pin 20 with a head 21, and a hook of this kind is engaged with each wing 12 which forms an aperture 22 receiving the pin. An adhesive layer 23 e.g. an adhesive tape, covers one side of the hook, and the male or hook part 24 of a Velcro type fastener is attached to the hook by means of the adhesive layer, FIG. 7. However, a narrow strip 25 of the hook is left free from the male part 24 of the Velcro type fastener A plate 26, FIGS. 8 and 9, comprises the female or loop part of the Velcro type fastener and one side thereof is provided with a layer 27 of a skin friendly adhesive or adhesive tape which is covered by a liner 28. Plate 26 (the female part of the Velcro type fastener) and adhesive 27 are soft and flexible and preferably are perforated by micropores in order to allow humidity to pass therethrough when the plate is attached to the skin.

Figure 5:
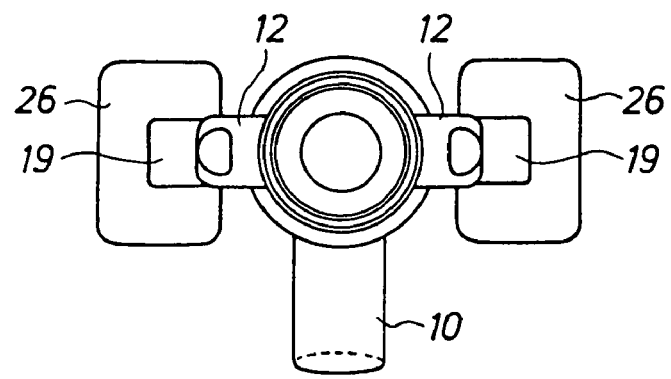
FIG. 5 is a front view of the device in FIG. 3 provided with adhesive plates.
Figure 6:
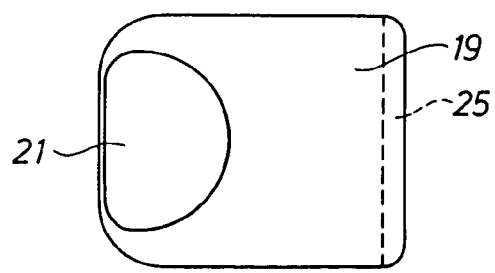
FIG. 6 is a plan view of a hook forming part of the device of the invention in the embodiment disclosed in FIGS. 3 to 5.
Figure 7:
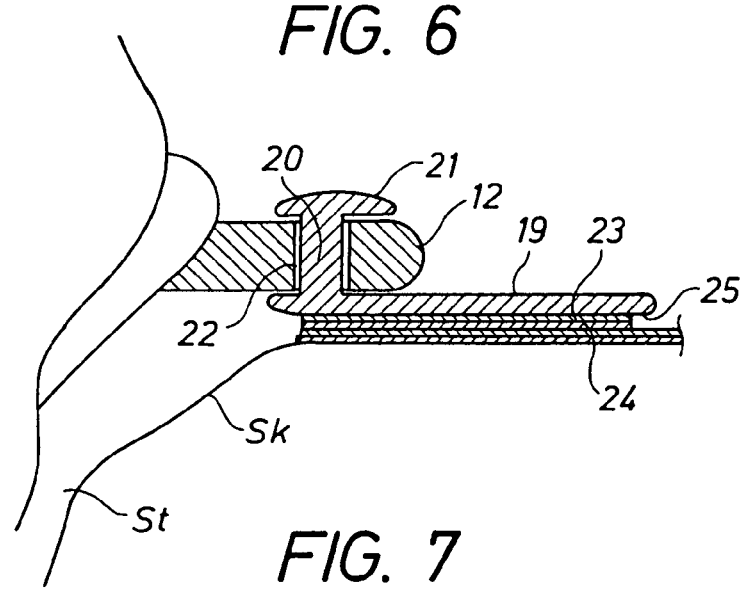
FIG. 7 is a longitudinal cross sectional view of the hook in FIG. 6.
Figure 8:
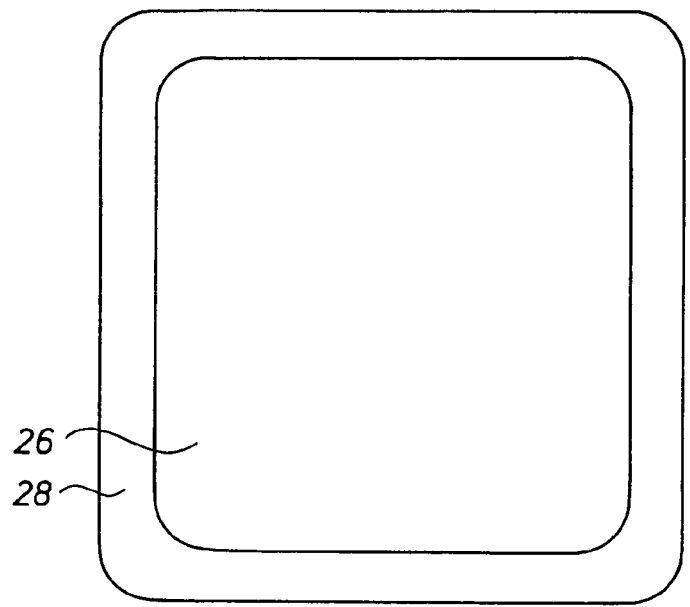
FIG. 8 is a plan view of an adhesive plate as shown in FIG. 5.
Figure 9:
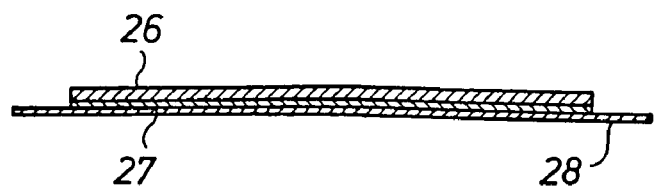
FIG. 9 is a cross sectional view of the adhesive plate in FIG. 8.

The male part 24 of the Velcro type fastener is engaged with the female part 26 of the Velcro type fastener in order to connect plates 26 with the hooks 19 as disclosed in FIG. 5. The liner 28 is removed from the adhesive layer 27 and the tracheal cannula 10 is attached to the skin Sk of the person's neck spaced from the tracheostoma St, FIG. 7.

The Velcro type fastener allows the tracheal cannula to be easily removed without it being necessary to loose the plates 26 from the skin, which makes manipulation of the cannula easier. Lifting of hook 19 from plate 26 at separation of the parts of the Velcro type fastener is facilitated by strip 25 a finger nail being inserted under said strip. The Velcro type fastener can be replaced by any other suitable fastener which allows the hooks to be easily connected with the plates and separated therefrom.

Figure 10:
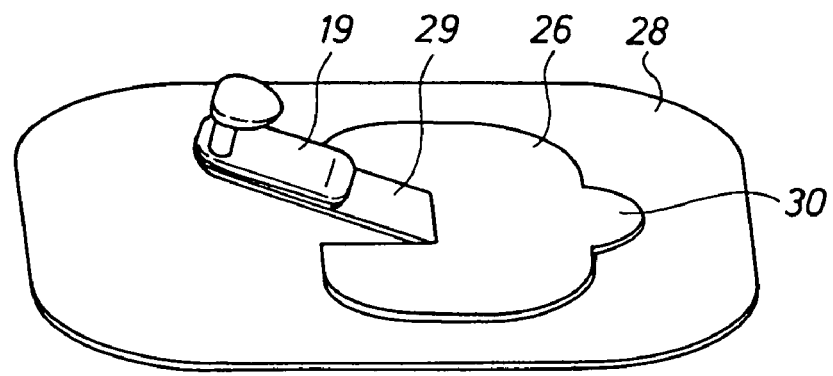
FIG. 10 is a perspective view of an adhesive plate mounted on a liner and provided with the hook of FIGS. 3 to 5.

In the embodiment of FIG. 10 the plate 26 forms a tongue or strip 29 to which hook 19 is attached permanently by welding or gluing or detachably by means of the Velcro type fastener. A flap 30 without adhesive facilitates removal of plate 26 from liner 28.

Figure 11:
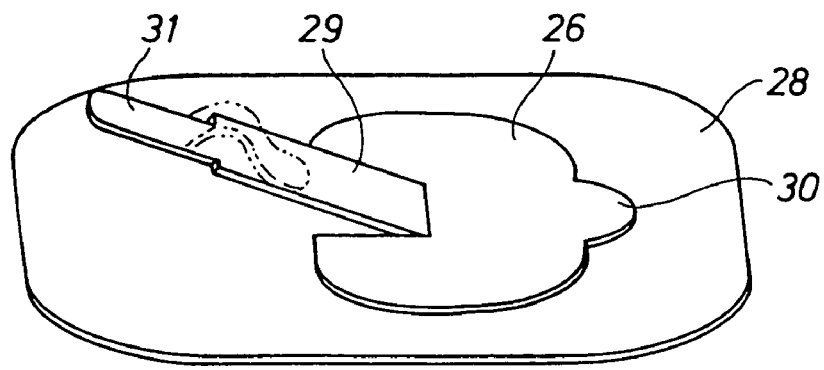
FIG. 11 is a perspective view as that in FIG. 10 of a modified embodiment of the means for connecting the adhesive plate to the tracheal cannula.

FIG. 11 discloses another embodiment in which hooks 19 are replaced by a narrow end portion 31 of strip 29. End portion 31 is provided with glue and after having been passed through aperture 22 in wing 12 is bent over and connected with the rest of strip 29 as indicated by dot-and-dash lines in FIG. 11.

In a further embodiment (not shown) plate 26 lacks the Velcro type fastener and is replaced by a flexible sheet which has the adhesive layer 27 on one side thereof. The plate is permanently connected with wing 12 e.g. by means of a strip 29 as disclosed in FIG. 11. In that case the adhesive plate must be removed from the skin each time the tracheal cannula shall be manipulated. However, it is also possible to have a Velcro type connection between end portion 31 and the rest of strip 29.

The invention claimed is:

1. A system for supporting and retaining an appliance on a person's neck in connection with a tracheostoma comprising:
   two wings, connected to the appliance, projecting in opposite directions from the appliance;
   the wings having a skin adhesive element each connected thereto, each skin adhesive element including a hook for connecting the skin adhesive element to the respective wing, each hook including a pin extending outward from the skin adhesive element and terminating in a head having a larger cross-section than the pin, wherein the pin of the hook engages an aperture in the corresponding wing when the skin adhesive element is attached to the wing; and
   a skin adhesive surface on each of the skin adhesive elements, distanced from the appliance, a space being provided between the adhesive surface and the tracheostoma.

2. The system of claim 1 wherein the appliance comprises a tracheal cannula.

3. The system of claim 1 wherein each skin adhesive element is detachably connected with the associated wing.

4. The system of claim 3 wherein the detachable connection between each skin adhesive element and the associated wing comprises the hook on the skin adhesive element detachably engaging the associated wing.

5. The system of claim 4, wherein the skin adhesive element is permanently connected with the associated hook.

6. The system of claim 1, further comprising a hook and loop type connection between each skin adhesive surface and the associated skin adhesive element.

7. The system of claim 6, wherein one part of each hook and loop type connection is attached to the associated skin adhesive surface.

8. The system of claim 6, wherein the other part of each hook and loop type connection is laminated with a liner and an adhesive therebetween.

9. The system of claim 1, wherein each skin adhesive element is permanently connected with the associated wing.

10. The system of claim 1, wherein the two wings terminate at an area adjacent to and on opposite sides of the appliance.

11. The system of claim 1, wherein the skin adhesive surface and the head of the hook are arranged on opposite sides of the wing when the skin adhesive element is attached to the corresponding wing.

12. The system of claim 1, wherein the head of the hook is displaced away from the skin adhesive element when the skin adhesive element is attached to the corresponding wing.

13. The system of claim 1, wherein the skin adhesive surface is detachably connected to the skin adhesive element to enable the skin adhesive element to be completely separated from the skin adhesive surface while maintaining the connection between the skin adhesive element and the corresponding wing.

14. The system of claim 13, wherein the detachable connection between the skin adhesive element and the skin adhesive surface includes a hook and loop type connector.

15. A system for supporting and retaining a tracheal cannula on a person's neck in connection with a tracheostoma comprising
   two wings, connected to the tracheal cannula, projecting in opposite directions from the cannula;
   the wings having a skin adhesive element each connected thereto;
   a detachable connection between the skin adhesive element and the associated wing including a pin extending outward from the skin adhesive element and terminating in a head having a larger cross-section than the pin, and an aperture formed in the corresponding wing, the pin of the hook detachably engaging the aperture in the corresponding wing when the skin adhesive element is attached to the wing; and a skin adhesive surface on each of the skin adhesive elements, distanced from the tracheal cannula, a space being provided between the adhesive surface and the tracheostoma.

16. The system of claim 15, wherein the two wings are separate and do not interconnect one another.

17. A system for supporting and retaining an appliance on a person's neck in connection with a tracheostoma, the system comprising:

a first wing and a second wing fixedly attached to the appliance, the first and second wings arranged on opposite sides of the appliance and extending radially outward from the appliance;

a first skin adhesive element detachably connected to the first wing and a second adhesive element detachably connected to the second wing, each skin adhesive element including a hook for detachably connecting the skin adhesive element to the respective wing, each hook including a pin extending outward from the skin adhesive element and terminating in a head having a larger cross-section than the pin, the pin engaging an aperture in the respective wing when the skin adhesive element is attached to the corresponding wing; and a first skin adhesive surface detachably connected to the first skin adhesive element, and a second adhesive surface detachably connected to the second skin adhesive element, the detachable connection enabling the first and second skin adhesive surfaces to be completely separated from the correspond skin adhesive elements, while maintaining the connection between the first and second skin adhesive elements and the corresponding wing.

* * * * *